US00PP16433P3

(12) United States Plant Patent
Shibamichi

(10) Patent No.: US PP16,433 P3
(45) Date of Patent: Apr. 11, 2006

(54) ***TILIA CORDATA* PLANT NAMED 'SHIBAMICHI GOLD'**

(50) Latin Name: *Tilia cordata*
Varietal Denomination: Shibamichi Gold

(75) Inventor: Akira Shibamichi, Kawasguchi (JP)

(73) Assignee: Hines Nurseries, Inc., Irvine, CA (US)

( * ) Notice: Subject to any disclaimer, the term of this patent is extended or adjusted under 35 U.S.C. 154(b) by 81 days.

(21) Appl. No.: 10/246,876

(22) Filed: Sep. 18, 2002

(65) Prior Publication Data

US 2004/0055063 P1 Mar. 18, 2004

(51) Int. Cl.
*A01H 5/00* (2006.01)

(52) U.S. Cl. ..... Plt./222

(58) Field of Classification Search ..... Plt./222
See application file for complete search history.

*Primary Examiner*—Kent Bell
(74) *Attorney, Agent, or Firm*—Christie, Parker & Hale, LLP

(57) ABSTRACT

A new plant variety of *Tilia cordata* Mill. named 'Shibamichi Gold' having bright golden yellow new foliage that matures to chartreuse in the summer.

2 Drawing Sheets

Classification: The present invention relates to a new *Tilia cordata* Mill. plant.

Varietal denomination: The new variety has the varietal denomination 'Shibamichi Gold'.

BACKGROUND OF THE INVENTION

The present invention relates to a new and distinct variety of *Tilia cordata* Mill., which was developed in a controlled program in Kawasguchi City, Japan by the originator Mr. Akira Shibamichi.

The genus *Tilia* comprises about 45 species of deciduous trees native to Eastern and Central North America; Europe; and Western Central and Eastern Asia. It is included in the family Tiliaceae which comprises about 48 genera and 725 species.

*Tilia cordata* is widespread and common throughout much of England, Wales, Northest Spain, Sweden to Western Russia and Southern Caucasia. It generally grows to 30 meters tall. Leaf color is deep green depending on light intensity and cultural conditions. Leaves are generally suborbicular, abruptly acuminate, finely and scabrous serrate on the margins. Leaves are generally glossy, dark green above, glaucescent with tufts in vein axils beneath. Flower color is yellowish white, fragrant in pendulous to erect cymes.

SUMMARY OF THE INVENTION

The new variety was discovered as a whole plant mutation in a controlled planting of *Tilia cordata* (unnamed, unpatented) and differs from it by having bright gold yellow new foliage that matures to chartreuse in the summer. Asexual reproduction of the new variety by grafting, has confirmed that the distinctive characteristics of the new variety are stable and transmitted to succeeding generations, and the new variety reproduces true to type.

COMPARISON WITH THE UNNAMED, UNPATENTED *TILIA CORDATA* PLANT

'Shibamichi Gold' is distinguished from it and all other varieties of *Tilia cordata* of which I am aware by its bright golden yellow new foliage which matures to chartreuse. In comparison, foliage of the the unnamed, unpatented *Tilia cordata* plant emerges green and remains green through maturity.

BRIEF DESCRIPTION OF THE ILLUSTRATIONS

The accompanying illustrations show a specimen of the new cultivar in photographic illustrations as true to color as is reasonably possible to make in illustrations of this character.

DETAILED DESCRIPTION OF THE INVENTION

Figure 1:
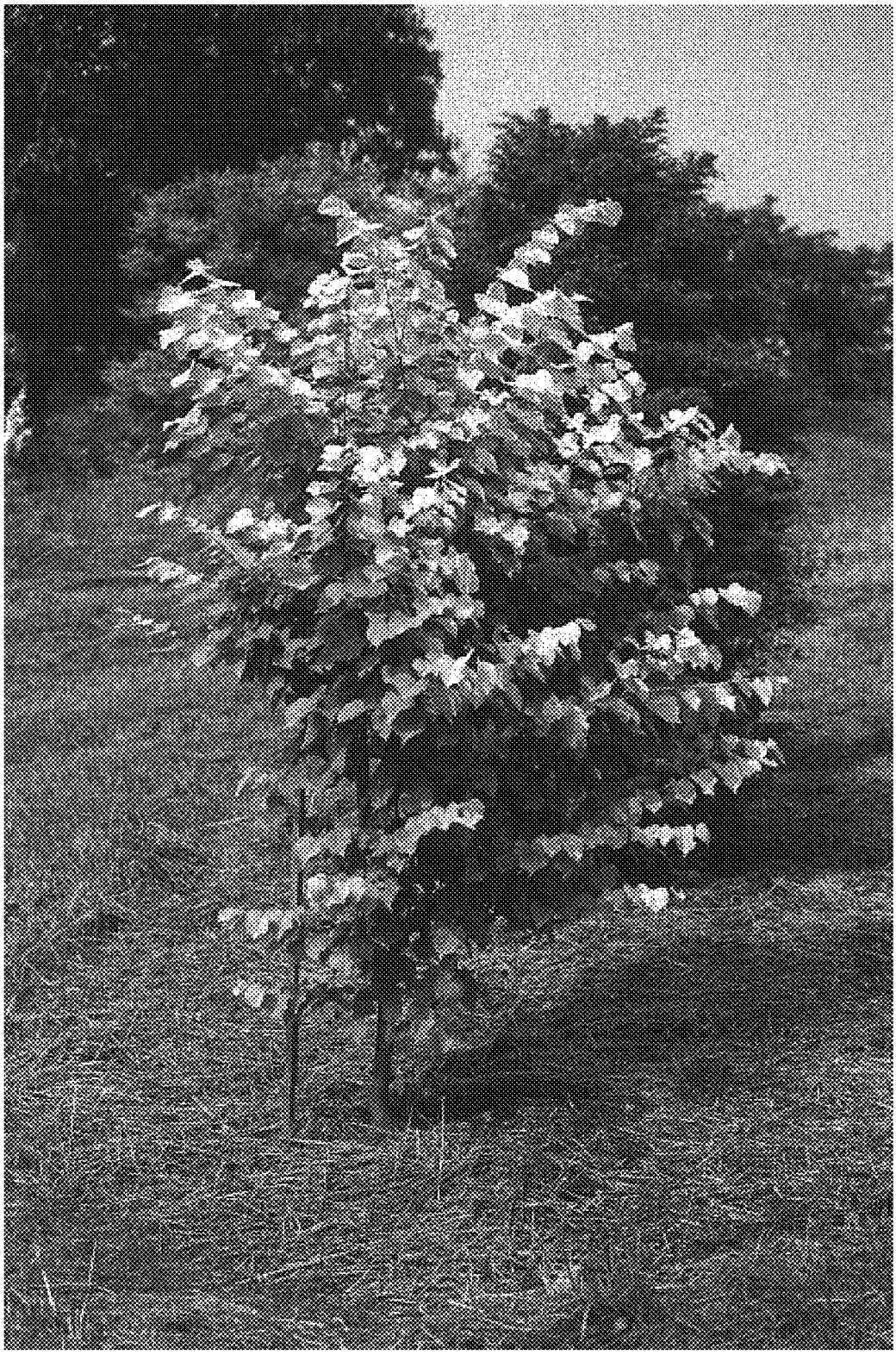
FIG. 1 shows the habit and the distinctive bright golden yellow new foliage and the darker chartreuse colored mature foliage of the new variety.
Figure 2:
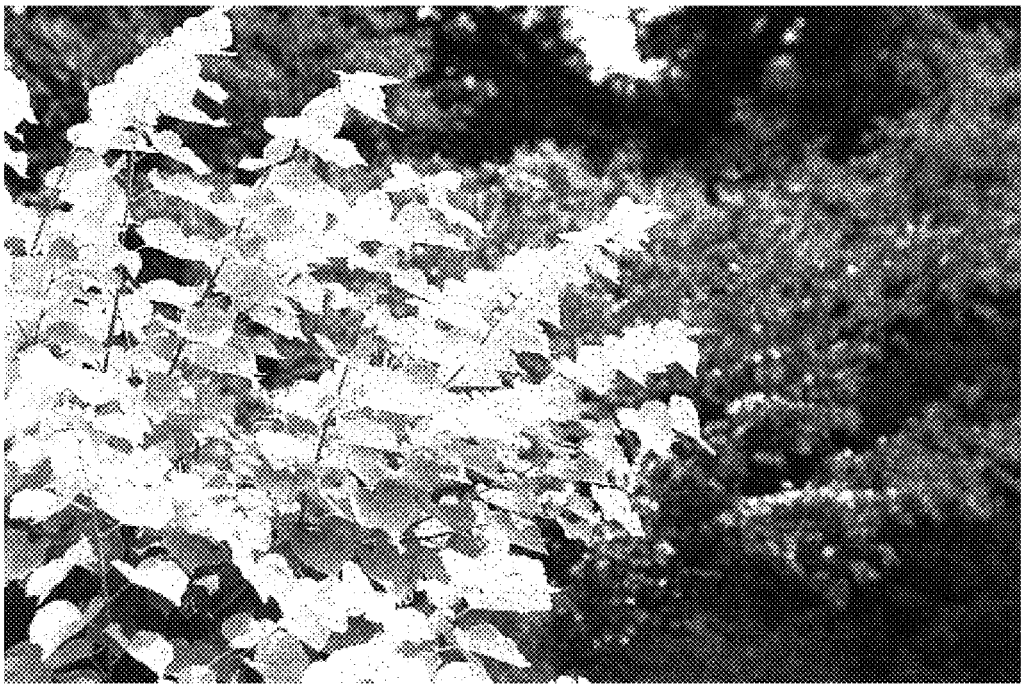
FIG. 2 shows a close-up view of the new foliage of 'Shibamichi Gold' showing its distinctive bright golden yellow color.

'Shibamichi Gold' has not been observed under all possible environmental, cultural and light conditions. The following observations and descriptions are of plants of an 8-year-old specimen grown in York Haven, Pa., in full sun, on a south-facing hillside, in decomposed sandstone loam soil. In this description, color references are to The Royal Horticultural Society Colour Chart (2001) and terminology used in the color descriptions herein refers to plate numbers in this color chart. Phenotypic expression may vary with light intensity, cultural and environmental conditions.

Plant:

*Size.*—About 5 meters tall, 3.75 meters wide.

*Age.*—About 8-years-old, in controlled trial conditions.

*Hardiness.*—USDA Zone 3 (−40° F. to −30° F.).

*Vigor.*—Rapid grower; approximately 0.5 meter per year.

*Habit.*—Upright spreading outward.

*Pests/diseases.*—None noted.

*Bark.*—Near Brown Group N200B.

*Branching.*—12 main branches with 10 to 15 subsidiary branches.

*Branch length.*—About 1.5 meters.

*Branch diameter.*—Up to about 8 cm at base; approximately 1 mm at apex.

*Color.*—New Shoots Upper Surface near Greyed-Orange Group 170A. Under Surface near Yellow Group 151B. Color of Apices: Near Greyed-Orange Group 165B.

*Mature shoots.*—Near Greyed-Orange Group 177C.

*Old wood.*—Abaxial: Near Greyed-Orange Group 165A. Adaxial: Near Greyed-Orange Group 166A.

*Trunk.*—Observed trunk diameter is approximately 10 cm at 60 cm above ground level. This is the point where the trunk is separated into multiple trunks. The ultimate dimensions are not known.

Leaf:

*Shape.*—Suborbicular to rounded cordate, apex is abruptly acuminate.

*Size.*—Length: Between 6.0 and 8.0 cm. Width: Between 6.5 and 8.0 cm.

*Leaf blade.*—Approximately 6 to 10 cm long, mostly around 7 cm, and 6 to 10 cm across, mostly around 7 cm.

*Leaf base.*—Cordate, mostly not deeply cordate, to nearly truncate.

*Leaf apex.*—Acuminate.

*Leaf margin.*—Serrate.

*Arrangement.*—Alternate.

*Texture/substance.*—Pubescent.

*Color.*—The following color readings are of mature specimens grown in York Haven, Pa. Young Foliage Upper Surface near Yellow-Green Group 151A to 151B; Under surface near Yellow-Green Group 145A. Mature Foliage Upper Surface near Green Group 143A; Under surface near Green Group 143C to 143D.

*Venation.*—Pattern: Upper surface, pinnate.

*Petioles.*—Size: Approximately 3 to 7 cm in length, mostly about 5 cm; width approximately 1.5 cm. Coloration: Near Yellow-Green Group 145B. Texture: Pubescent.

*Internode length.*—Between 2.5 and 3.7 cm.

Inflorescence: Due to the immaturity of the plant, no flowers have been produced. Flower production would not be expected until at least the $10^{th}$ year of growth.

I claim:

1. A new and distinct variety of *Tilia cordata* plant as shown and described.

* * * * *